(12) United States Patent
Chawla et al.

(10) Patent No.: US 8,504,343 B2
(45) Date of Patent: Aug. 6, 2013

(54) DISEASE DIAGNOSES-BASES DISEASE PREDICTION

(75) Inventors: Nitesh V. Chawla, Granger, IN (US); Albert-Laszlo Barabasi, Brookline, MA (US); Nicholas Christakis, Concord, MA (US)

(73) Assignees: University of Notre Dame du Lac, Notre Dame, IN (US); President and Fellows of Harvard College, Cambridge, MA (US)

( * ) Notice: Subject to any disclaimer, the term of this patent is extended or adjusted under 35 U.S.C. 154(b) by 1245 days.

(21) Appl. No.: 12/023,935

(22) Filed: Jan. 31, 2008

(65) Prior Publication Data

US 2008/0183454 A1  Jul. 31, 2008

Related U.S. Application Data

(60) Provisional application No. 60/898,739, filed on Jan. 31, 2007.

(51) Int. Cl.
*G06G 7/58* (2006.01)

(52) U.S. Cl.
USPC ............................................. 703/11

(58) Field of Classification Search
USPC ............................................. 703/11
See application file for complete search history.

(56) References Cited

U.S. PATENT DOCUMENTS

| | | | |
|---|---|---|---|
| 6,110,109 A | 8/2000 | Hu et al. | |
| 6,353,813 B1 * | 3/2002 | Breese et al. | 706/12 |
| 2004/0015337 A1 | 1/2004 | Thomas et al. | |
| 2006/0064415 A1 * | 3/2006 | Guyon et al. | 707/6 |
| 2006/0218010 A1 * | 9/2006 | Michon et al. | 705/3 |
| 2007/0208545 A1 | 9/2007 | Wittkowski | |
| 2008/0059224 A1 | 3/2008 | Schechter | |

* cited by examiner

*Primary Examiner* — Jerry Lin

(74) *Attorney, Agent, or Firm* — Knobbe, Martens, Olson & Bear, LLP

(57) ABSTRACT

A system for predicting future disease for a subject comprising: a population information set comprising population disease diagnoses for members of a population; a subject-specific information set comprising at least one subject-specific disease diagnosis; and a diagnoses-based prediction module configured to predict one or more future diseases for the subject based on said subject-specific disease diagnosis and said population disease diagnoses for population members having at least one disease in common with the subject.

33 Claims, 14 Drawing Sheets

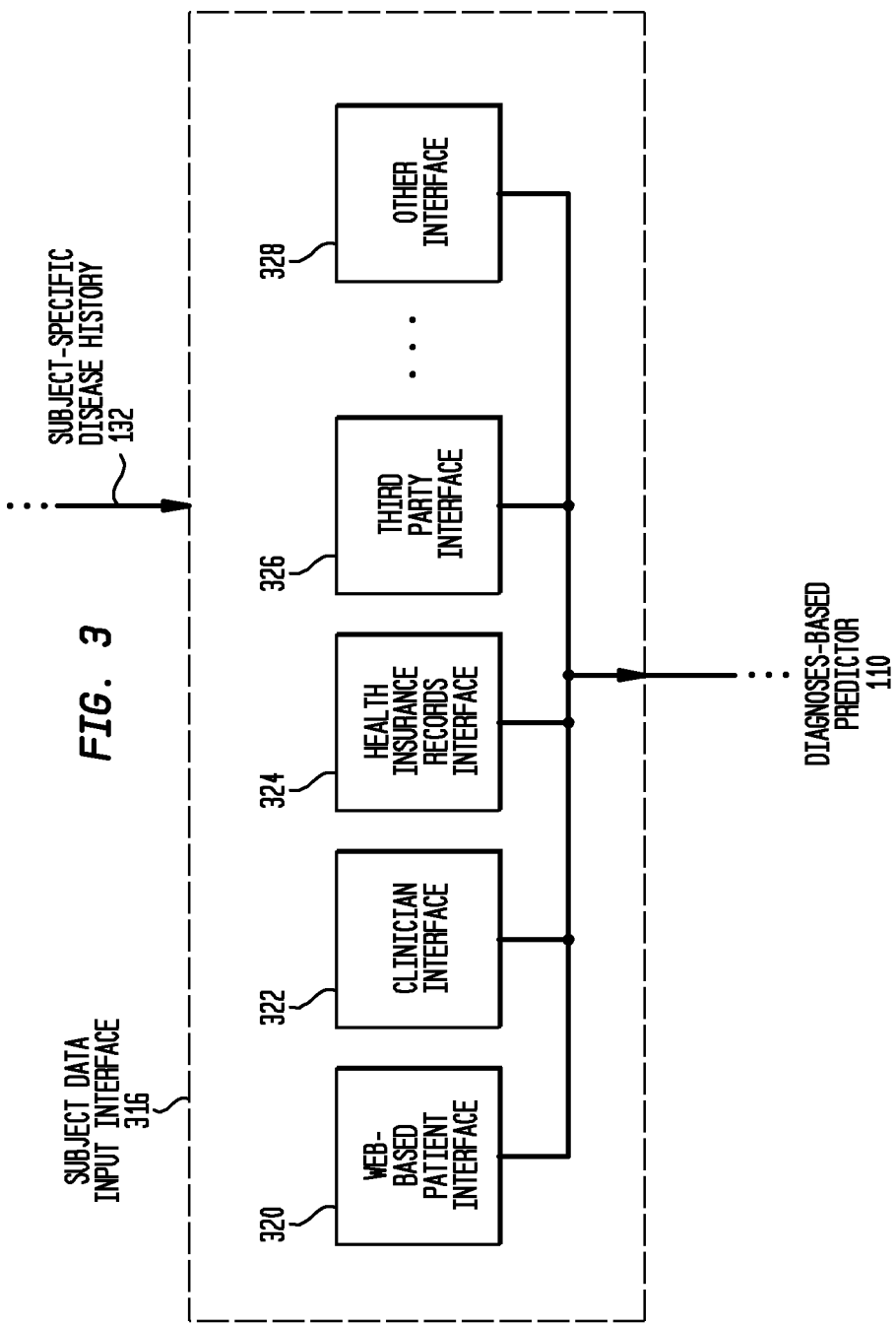

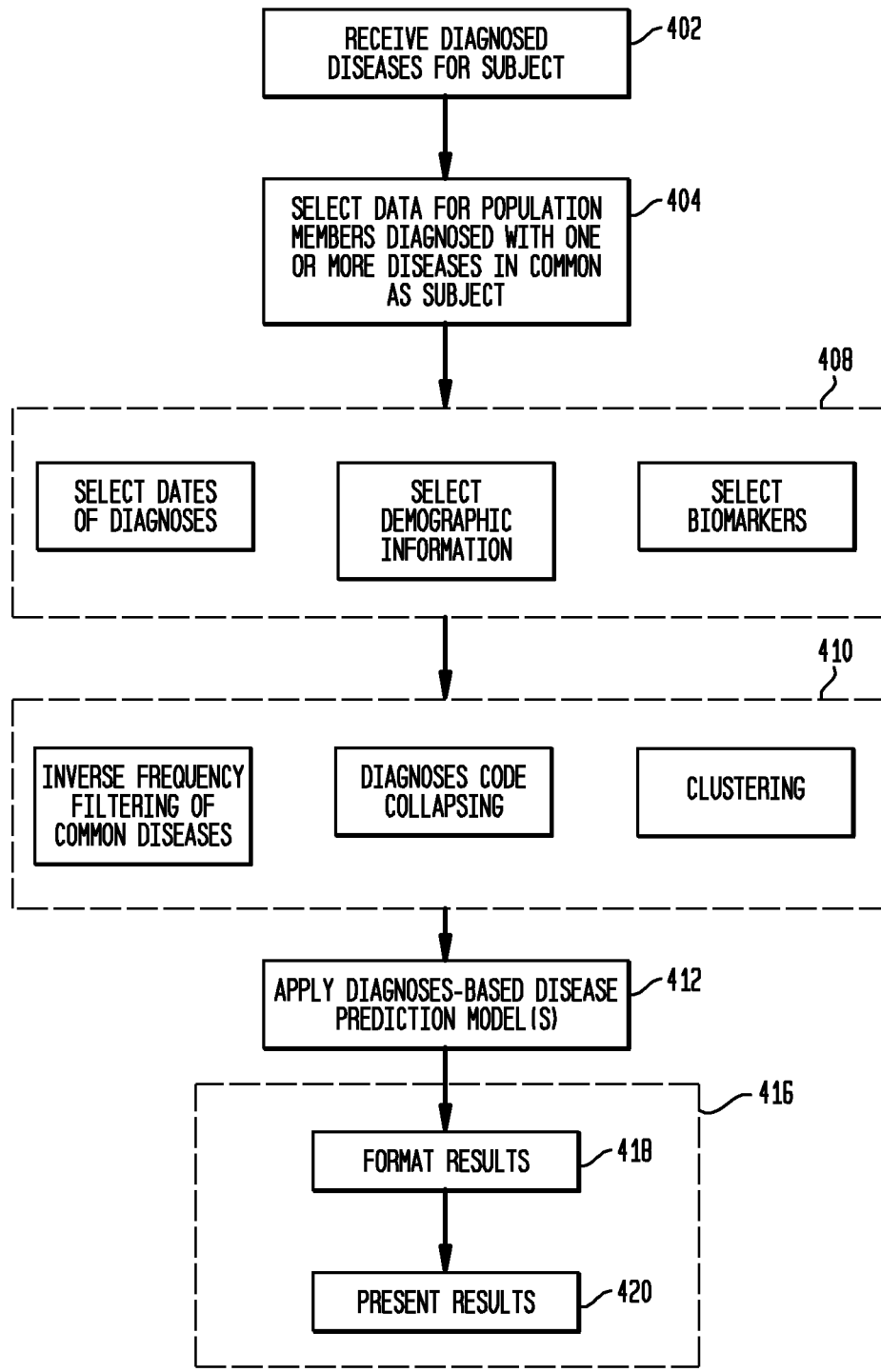

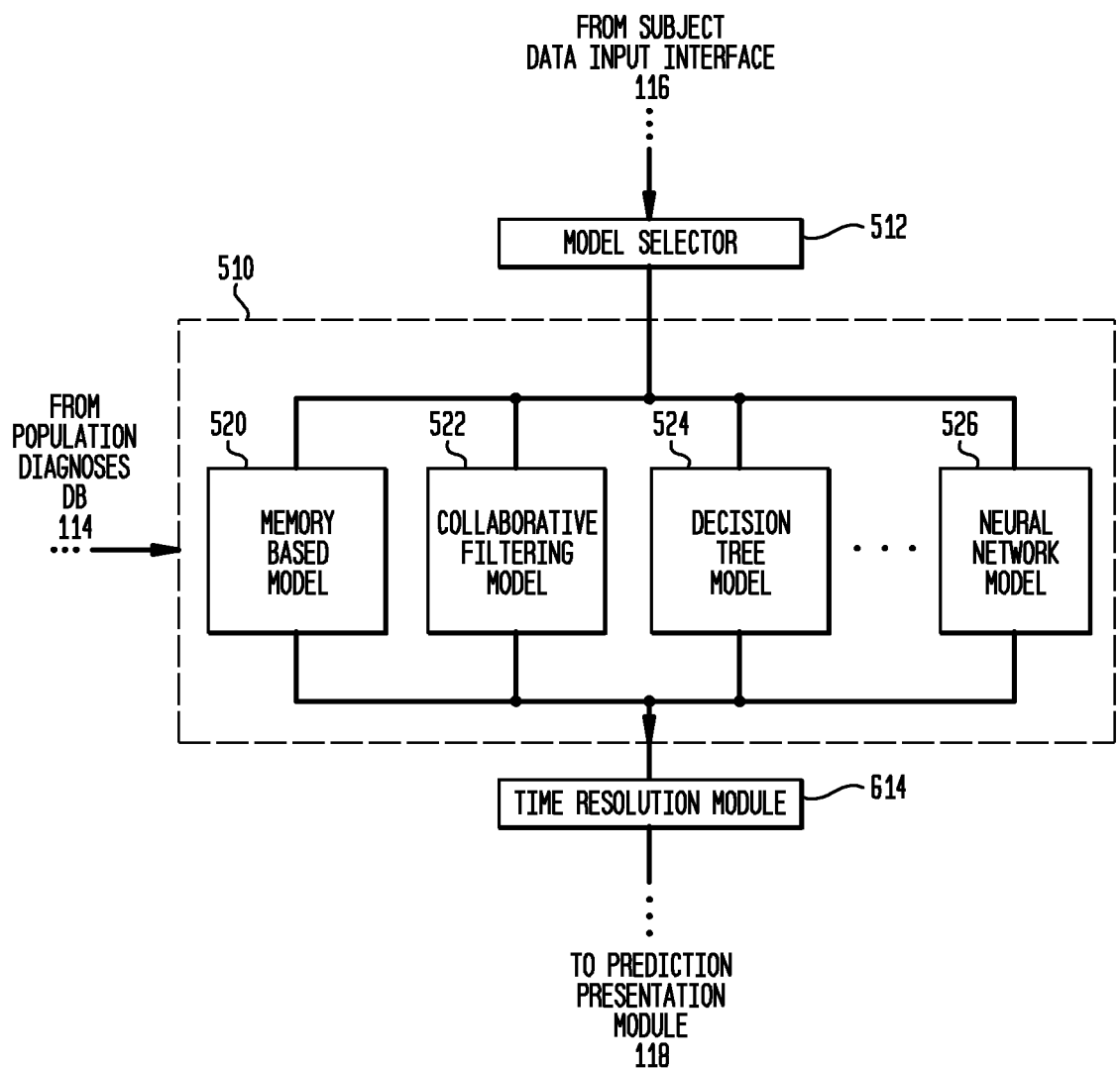

FIG. 7A 730

"DASHBOARD-INDIVIDUAL INFO ENTRY"

732

NAME: JANE SMITH   DOB: 11-21-1980
HOME ADDRESS: 123 NANTUCKET LN   ZIP: 28419

ENTRY OPTIONS:
734
- ⦿ BY ICD-9/10 CODE LOOKUP   ○ ALPHABETICAL LIST
- ○ INTERVIEW WIZARD   ○ NATURAL LANGUAGE ENTRY
- ○ ELECTRONIC RECORDS DOWNLOAD

FIG. 7B 736

"DASHBOARD-INFO ENTRY BY ICD-9/10 CODE"

740
⦿ BY ICD-9   ○ BY ICD-10

742
ENTER CODE: [    ]

NAVIGATE CODES
- ⊞ 0-100
- ⊞ 101-200
- ⊞ 201-300
- ⊞ 301-400

744
[ SEARCH ]

746

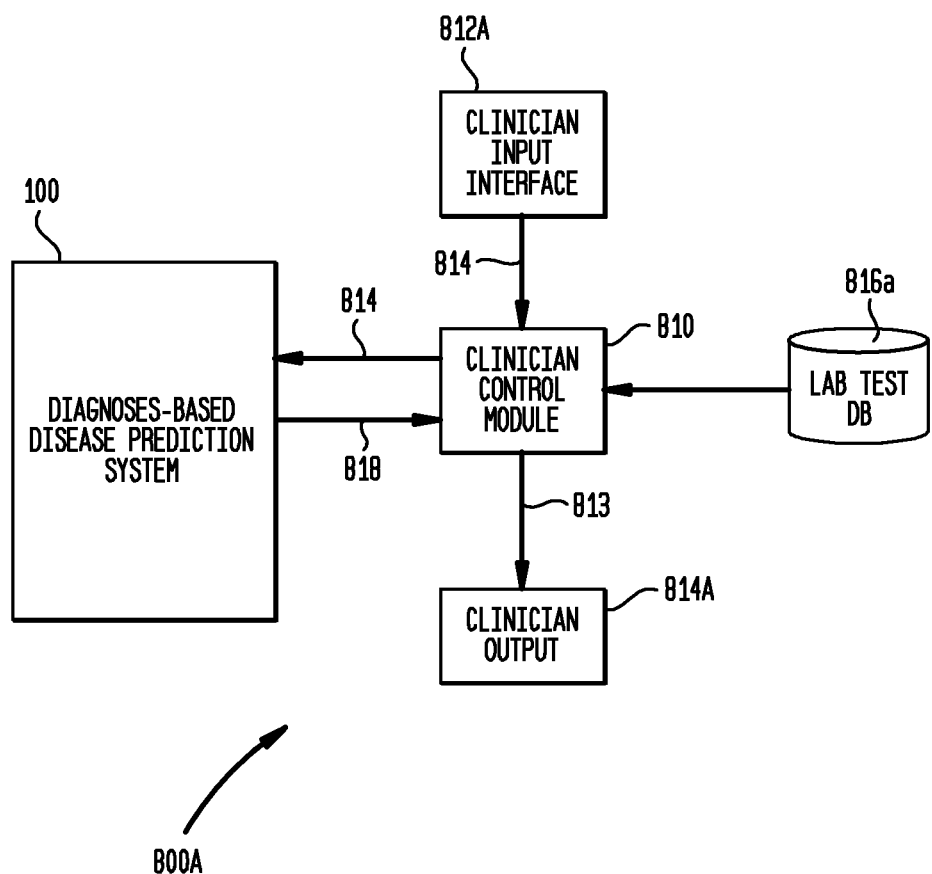

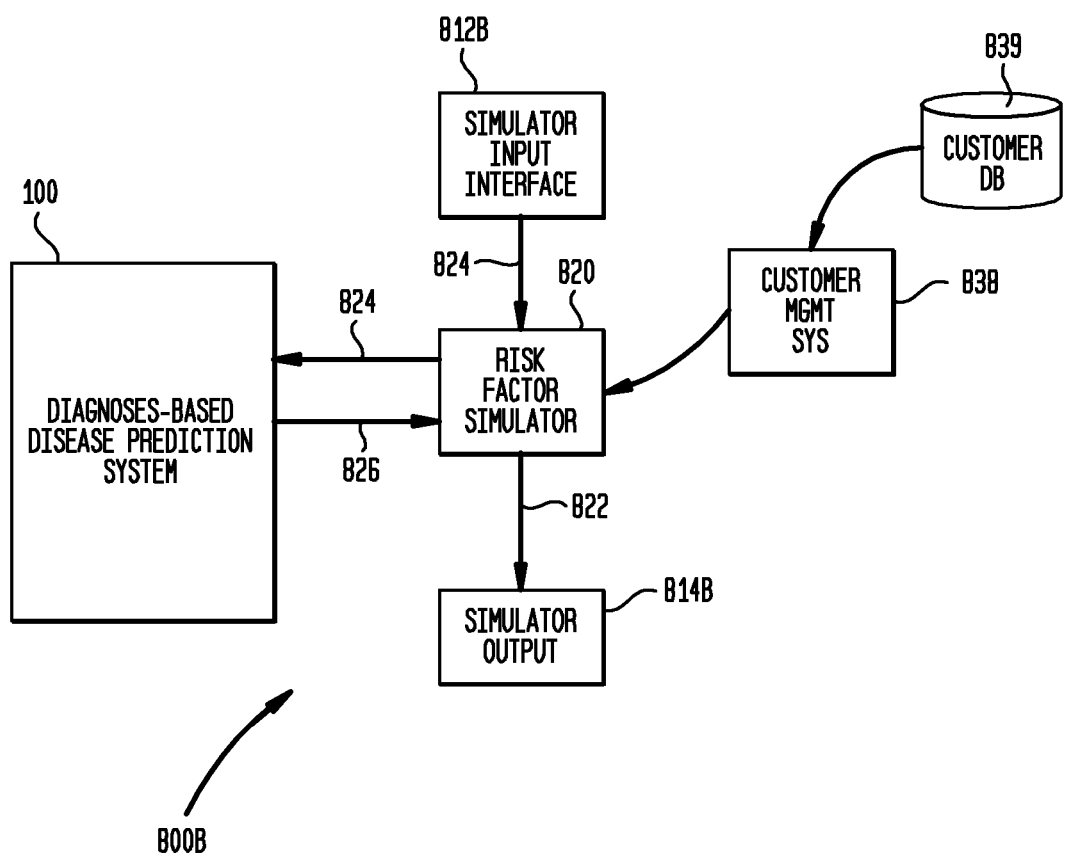

DISEASE DIAGNOSES-BASES DISEASE PREDICTION

CROSS-REFERENCE TO RELATED APPLICATIONS

This application claims the benefit of U.S. Provisional Application No. 60/898,739 entitled "Disease Prediction Using Collaborative Filtering" filed Jan. 31, 2007. The entire disclosure and contents of the above application is hereby incorporated by reference herein.

BACKGROUND

1. Field of the Invention

The present invention relates generally to disease prediction, and more particularly, to a disease diagnoses-based disease prediction system.

2. Related Art

In the medical field, diagnoses of existing diseases for a subject (also referred to herein as "patient") are generally made by a clinician, such as a physician, veterinarian, or other health care provider, based on a variety of information, including interviews, examinations and tests of the subject. These interviews, examinations and tests may be conducted over a period of time, during which notes and records about such events are generated and retained. The tests may include analysis of biological fluids drawn or received from the subject, such as blood or urine, for signs and/or symptoms (also referred to herein as "biomarkers") of one or more diseases. However, the interpretation of such interviews, examinations and test results involve the subjective analysis by the clinician which may result in an inaccurate diagnosis.

Even when a subject is correctly diagnosed with a disease, such interviews, examinations and tests fail to directly provide information about diseases which the subject may have in the future. The prediction of the subject's future diseases has traditionally involved a trained clinician's use of general medical knowledge or studies regarding the interrelationships between diseases, for example patterns recognized in which the diagnosis of an existing disease in a subject appears to occur prior to the occurrence of other diseases. As with interpreting information such as biomarkers, this application of medical knowledge is subjective and may vary from clinician to clinician. Another proposed method for predicting a subject's future diseases is to create a large collection of biomarkers and associate diseases, and then to apply pattern recognition systems to the subject's biomarkers in order to predict future diseases for a particular subject.

SUMMARY

According to one aspect of the present invention, there is provided a system for predicting future disease for a subject comprising: a population information set comprising population disease diagnoses for members of a population; a subject-specific information set comprising at least one subject-specific disease diagnosis; and a diagnoses-based prediction module configured to predict one or more future diseases for the subject based on said subject-specific disease diagnosis and said population disease diagnoses for population members having at least one disease in common with the subject.

In another aspect of the present invention, there is provided a method for predicting future disease for a subject based on a population information set containing population disease diagnoses for members of a population; and a subject-specific information set containing at least one subject-specific disease diagnosis, comprising: generating one or more disease predictions for the subject based on said subject-specific disease diagnosis and said population disease diagnoses for population members having at least one disease in common with the subject.

In yet another aspect of the present invention, there is provided a system for predicting future disease for a subject based on a population information set containing population disease diagnoses for members of a population; and a subject-specific information set containing at least one subject-specific disease diagnosis, comprising: means for generating one or more disease predictions for the subject based on said subject-specific disease diagnosis and said population disease diagnoses for population members having at least one disease in common with the subject.

BRIEF DESCRIPTION OF THE DRAWINGS

Embodiments of the present invention will be described in conjunction with the accompanying drawings, in which:

FIG. 3 is a block diagram of the subject data input interface as illustrated in FIG. 1, in accordance with one embodiment of the present invention;

FIG. 4C is a flowchart illustrating one embodiment of the present invention in which diagnoses-based disease predictions are generated, including the use of non-diagnosis and other parameters utilized to generate the disease predictions;

FIG. 5 is a block diagram of a diagnoses-based prediction execution module configured to generate a disease prediction based on one of several available prediction models, in accordance with one embodiment of the present invention;

FIG. 7A is a simplified display of subject data input interfaces, in accordance with one embodiment of the present invention;

FIG. 7B is a simplified display of a yet further subject data input interfaces, in accordance with one embodiment of the present invention;

FIG. 8A is a block diagram of a clinician-operable application of the diagnoses-based disease prediction system illustrated in FIG. 1, according to one embodiment of the present invention;

FIG. 8B is a block diagram of a risk-factor modification application of the diagnoses-based disease prediction system illustrated in FIG. 1, according to one embodiment of the present invention;

DETAILED DESCRIPTION

The present invention is directed to predicting future onset of diseases in a subject based on past diagnoses of diseases of the subject and of a population. Specifically, this approach, referred to herein as a disease diagnoses-based prediction, receives past diagnosed diseases of the subject, accesses an information set such as a database containing diagnostic data for a plurality of population member to select members having one or more diseases in common as the subject, and then applies one or more prediction models using the diagnostic data of the selected members. More specifically, different prediction models may be utilized to generate the disease predictions, individually or simultaneously. The generated disease predictions may be ranked, filtered or otherwise modified to provide it in a form that is useful to the operator. As used herein, "diagnosis" refers to the identification or recognition of a disease or medical condition by the signs and symptoms gathered from, for example, interviewing, laboratory testing, and examining a subject. A non-diagnosis occurs when such interviewing, laboratory testing, and examining results in a determination that a disease or abnormal medical condition can not be recognized or identified.

Figure 1:
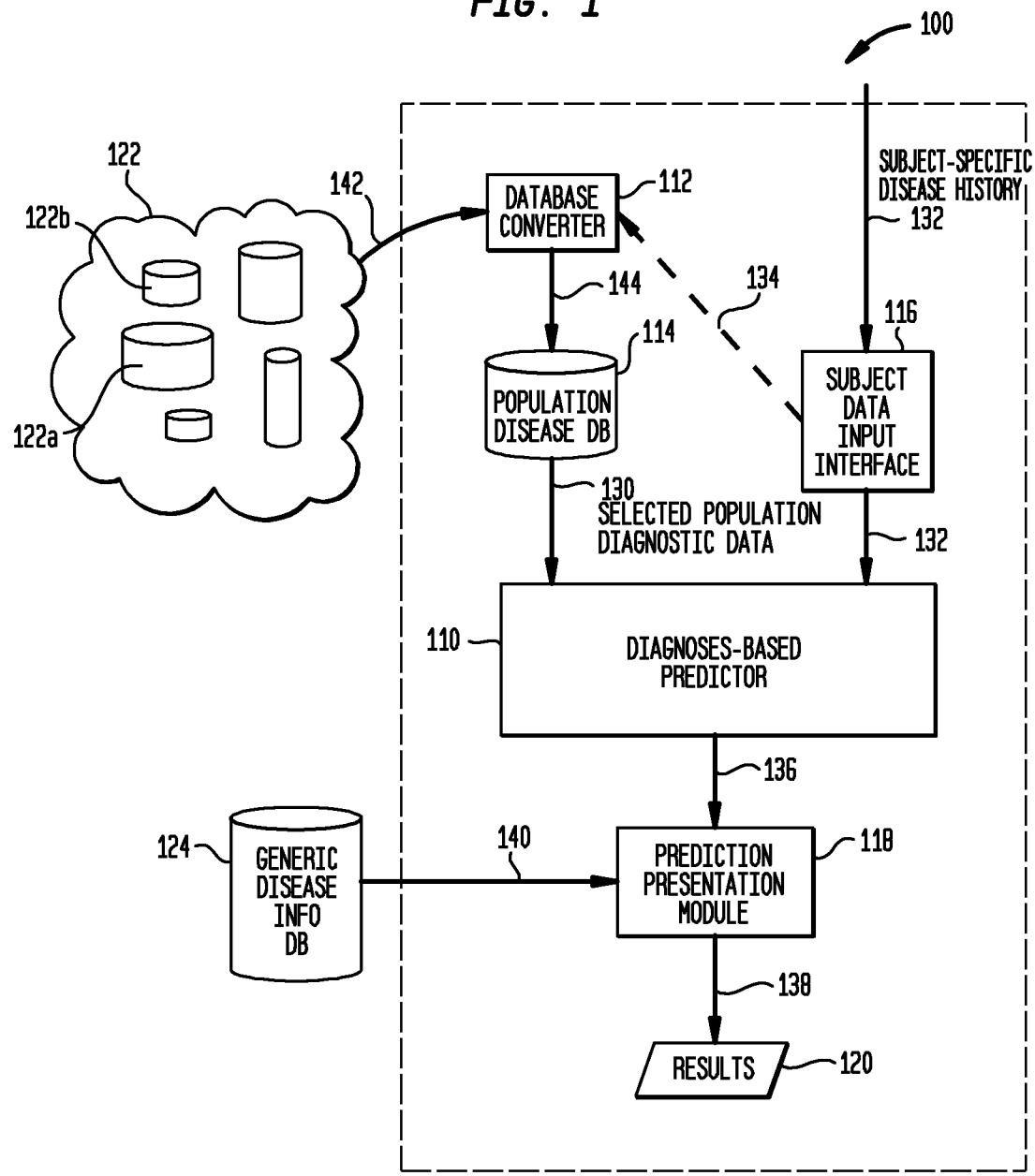
FIG. 1 is a block diagram of one embodiment of a diagnoses-based disease prediction system according to one embodiment of the present invention.

A block diagram of a diagnoses-based disease prediction system according to one embodiment of the present invention is illustrated in FIG. 1. Diagnoses-based disease prediction system 100 comprises a population diagnosed-disease database 114 and a subject data input interface 116. Database 114 contains disease diagnostic data about a population comprising a plurality of individuals (also database "members"). Database 114 should be sufficiently populated with enough diagnoses (also "diagnostic data") and other data for members, and with sufficient numbers of members in order to permit meaningful statistical interference to be applied which can yield useful results. As will be obvious to a person of ordinary skill in the art, the exact threshold number of diagnoses data and/or number of members will vary depending on the disease-prediction model being applied or on the disease or diseases being analyzed. The data for members of population diagnosed-disease database 114 may be anonymized or otherwise truncated or modified so that the data contained therein can not be used to personally identify the actual individual, in order to comply with Federal, state and local laws, regulations and guidelines concerning privacy of patient records, such as the Health Insurance Portability and Accountability Act ("HIPAA"). Subject data input interface 116 receives subject-specific disease history 132 from a user, such as the subject or clinician, a data conversion software interface, or from an output interface of a special-purpose application that is configured to provide information to diagnoses-based disease prediction system 100 and to receive the generated future disease predictions. Subject data input interface 116 may be configured to permit direct entry of information to diagnoses-based disease prediction system 100 through a software graphical user interface ("GUI") and an input device such as a keyboard and mouse (not shown). Alternatively, subject data input interface 116 may be configured to allow input to be transmitted from a remote location through a network connection, such as via the Internet (not shown).

In one embodiment of the present invention, population diagnosed-disease database 114 is populated with population disease diagnostic data 142 received from one or many databases and data sources 122. The variety and number of different data sources are represented as databases 122A and 122B, and may be sources of data from pre-existing database of disease diagnostic data, hospitals' patient databases, health insurance carriers' claims and or customer databases, among others. It is to be understood that although data is said to be stored in databases, other structures or systems for storing data may be used in other embodiments of the present invention. Furthermore, in alternative embodiments of the present invention, no databases or data sources 122 are used to populate population diagnosed-disease database 114. Instead, in those alternative embodiments, database 114 is created prior to, or during, implementation of system 100 data received interface 116. The format of the population disease diagnostic data 142 from these various databases 122 may be different with respect to one another, in addition to being different from the format of population diagnosed-disease database 114. Therefore, database converter 112 may be used to convert the population disease diagnostic data 142 from various databases 122 into a format consistent with database 114. Once converted, this converted population disease diagnostic data 144 is added to database 114. Additionally, in another embodiment of the present invention, it is beneficial to add subject-specific disease history 132 to database 114 in order to grow database 114, thereby improving its performance or accuracy. In order to do so, subject-specific disease history 132 is anonymized and/or formatted by submitting subject-specific disease history 132 to database converter 112 and then appending or updating database 114 with subject-specific disease history 132, now anonymized and/or formatted. Alternatively, in another embodiment of the present invention, subject data input interface 116 may be configured to select and provide only a subset of subject-specific disease history 132 such that the selected data maintains the anonymity of the subject.

In one embodiment of the present invention, a computer system (not shown) or a collection of computer system may be used for implementation purposes. As will be apparent to one of ordinary skill in the art, the population diagnosed-disease database 114 may be stored, accessed, or implemented in storage architecture such as a storage area network ("SAN") while the subject data input interface 116 may be provided via a computer that is remote from the SAN. Alternatively, where the database files containing population database 114 is sufficiently small in size and/or complexity, those database files may be stored and accessed via a single computer system that also provides access via input interface 116. Similarly, as would be appreciated by one or ordinary skill in the art, prediction presentation module 118 may be implemented on the same or different computer system as the system on which input interface 116 is provided. Furthermore, it is to be understood that a graphical user interface ("GUI") may be used in addition to the hardware normally associated with computer systems configured to receive user inputs.

As shown in FIG. 1, diagnoses-based predictor 110 receives subject-specific disease history 132. Using subject-specific disease history 132, predictor 110 selects members in population diagnosed-disease database 114 having diseases in common with those disease(s) in subject-specific disease history 132. Selected population diagnostic data 130 is received by diagnoses-based predictor 110 and used in conjunction with one or more prediction models, described in detail below, in order to generate raw diagnoses-based disease prediction data 136. Although embodiments of the present invention have been described in terms of using disease diagnostic information about a subject and members of population database 114, it is to be understood that non-diagnosis information about the subject and/or the population members may be used in addition to diagnosis information. For example, the fact that a population member was diagnosed for type-II diabetes and tested negatively for (or was not diagnosed with) Alzheimer's may be useful by an embodiment of the present invention in generating disease predictions for the subject.

Furthermore, although members of population diagnosed-disease database 114 have been discussed as a selection, it is to be understood that multiple selections or clusters of population members may be formed, wherein each cluster represents population members having a different set of one or more diseased in common with the subject. After forming the multiple clusters, the same or different predictions models, as described further herein, may be applied to each of the clusters based on the distribution and nature of the diseases in each cluster.

Prediction data 136 includes predictions about one or more diseases, which depends on the number and types of diseases entered as subject-specific disease history 132, on the members selected in selected population diagnostic data 130 and the diseases of those members which may eventually become one of the predicted diseases in prediction data 136, and the calculations by the one or more prediction models in diagnoses-based predictor 110. Prediction data 136 includes not only the identity of the predicted diseases, but may also include other information such as the probability of each predicted disease, disease names, International Statistical Classification of Diseases and Related Health Problems (e.g., ICD-9, ICD-9-CM, ICD-10, ICD-11). Raw diagnoses-based disease prediction data 136 is provided to prediction presentation module 118. Prediction presentation module 118 manipulates the information in prediction data 136 into organized results data 138 for presentation to the user of system 100 as presentation results 120. For example, prediction presentation module 118 may sort the predicted diseases into organized results data 138 based on the probabilities of occurrence, from highest to lowest, so that immediate attention may be given to the predicted diseases having the highest probabilities by displaying the most likely diseases at the top of presentation results 120. This may be especially valuable when a large number of diseases are included in organized results data 138, some having relatively low probabilities of occurrence.

Prediction presentation module 118 may incorporate generic information or documents 140 from other sources such as generic disease information database 124 and provide the incorporated information and documents in presentation results 120. The information incorporated may include descriptions about the predicted disease, for educational purposes, or may include network shortcuts or links, as are common in Internet browser navigation. Similarly, the documents incorporated from information database 124 may include journal articles about one or more predicted diseases or, in certain embodiments of the present invention, materials such as advertisements, coupons, and promotional materials which have nothing to do with the diseases predicted but which are presented to the user by presentation results 120.

Figure 2:
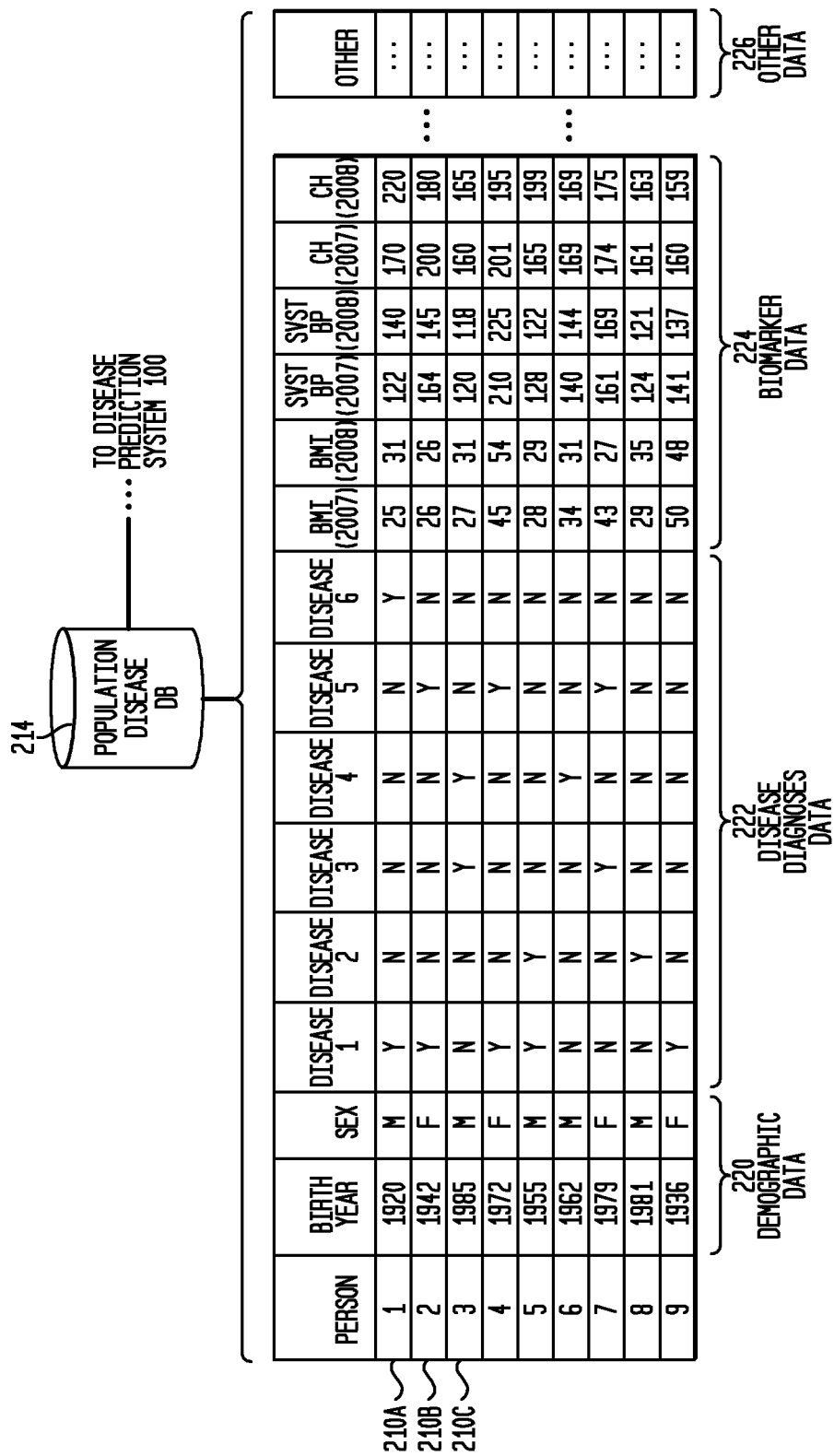
FIG. 2 is a schematic block diagram depicting a population diagnosed-disease database which embodiments of the present invention may utilize, in accordance with one embodiment of the present invention.

FIG. 2 is a schematic block diagram of one embodiment of the population diagnosed-disease database 114 illustrated in FIG. 1, referred to herein as population diagnosed-disease database 214. FIG. 2 depicts in table form exemplary contents of database 214, in accordance with one embodiment of the present invention. As illustrated in FIG. 2 and as noted above with reference to FIG. 1, in one embodiment, population diagnosed-disease database 214 provides disease diagnostic and other data to disease prediction system 100. At a minimum, it will have disease diagnostic data 222 which will be compared to the past diagnoses of the subject and used to predict future diseases for the subject. Database 214 may also include demographic data 220, biomarker data 224 and other data 226. Examples of demographic data 220 may include date of birth, gender, and other information about the subject. Examples of biomarker data 224 may include measurements of various bodily organs of the subject or signs and symptoms based on laboratory testing of biological fluids drawn or received from the subject, such as blood or urine. For example, biomarker data 224 may include a measure of body-mass-index based on the weight and height of the subject, the blood pressure of the subject, and cholesterol levels for the subject, as illustrated in FIG. 2 as biomarker data 224. As one of ordinary skill in the art would appreciate, the data referred to in FIG. 2 as biomarker data 224 may include data other than the types shown in FIG. 2. In addition to the diagnostic data and non-diagnoses data illustrated in FIG. 2, other data 226 may be contained in database 214. For example, secondary diagnoses of one or more diseases or ailments diagnosed at the time that the subject presents himself to a clinician complaining of the primary disease diagnosed, address or location where each diagnosis was made, the clinician making each diagnosis, treatment or intervention provided, status information about the treated disease, drugs administered, time information for a diagnosis, among others. It is to be understood that the "time information" included among other data 226 may be an exact date and/or time, just a year, a season (e.g., "spring 2008"), a quarter (e.g., "second quarter of 2008"), relative to the subject's age (e.g., diagnosed at subject_age=57), etc. Additionally, the time information may be a relative date, such as for example, relative to a date of diagnosis for a different disease (e.g., as time information for disease X, "X disease diagnosed 3 years after Y disease diagnosed"). It is to be understood that population diagnosed-disease database 114 may be incomplete in that some data for a particular member, for example gender data, may exist in database 114 for some members of the population represented in database 114 while not for other members. Furthermore, although population diagnosed-disease database 214 is depicted in FIG. 2 as a two-dimensional table in this embodiment, it is to be understood that other data structures are possible and are considered within the scope of other embodiments of the present invention. For example, a three-dimensional storage table or object oriented database structures may be used to organize and store the data described herein.

The data contained in population diagnosed-disease database 114 may be represented and stored in various ways, in alternative embodiments of the present invention. For example, FIG. 2 depicts population diagnosed-disease database 114 as storing "Y" (for yes) or "N" (for no) to indicate whether a population member has been diagnosed with the particular disease. In alternative embodiments, the diagnosis for each population member may be represented in terms of binary 0's and 1's. In one embodiment, information about a subject i having a diagnosis j may be stored a vector $v_{ij}$. If subject i has been positively non-diagnosed or determined not to have disease j, then $v_{ij}=0$ is stored in database 114. Where subject i has been diagnosed with disease j, then $v_{ij}=1$. Where subject i has not been tested for disease j, or when the results cannot be reliably interpreted, then $v_{ij}$ can be set as undefined, or may be set to a predefined value which may improve the prediction results. For example, where subject i has not been tested, $v_{ij}$ can be set to the generally accepted occurrence for that disease j for the general or a specific segment of the population. By setting $v_{ij}$ to an established occurrence, the non-diagnosis of $v_{ij}=0$ may be more useful in determining which diseases are not likely to occur in subject i, given the disease history of others in database 114.

Furthermore, where subject i has been diagnosed for disease j, $v_{ij}$ may be set to numbers others than 1, where those other numbers may signifies the severity or present condition of disease j diagnosed in subject i. For example, where there are five grades of severity for a disease j=X, one subject may be diagnosed as having j=X at grade 1, which may mean that only a small or non-serious condition of disease j=X was found in subject i. Thus, $v_{ij}$ for disease j=X may be recorded in database 114 as 0.2. However, another subject may have the same disease j=X, but may be diagnosed at grade 5, meaning that disease j=X is inoperable or untreatable and that subject i is expected to expire within 0-6 months. For this subject, $v_{ij}$ for disease j=X may be recorded in database 114 as 1.0. It should be appreciated that a general system for coding database 114 to include severity information as described above is implemented in the embodiment described. Thus, it will be obvious to one or ordinary skill in the art that vector $v_{ij}$ may be scalar, but may also be multi-valued.

FIG. 3 is a block diagram of one embodiment of the subject data input interface 116 illustrated in FIG. 1, referred to herein as subject data input interface 316. FIG. 3 depicts exemplary interfaces 320, 322, 324, 326 and 328, in accordance with one embodiment of the present invention. As noted, subject data input interface 116 receives subject-specific disease history 132 from a user, such as the subject or clinician and provides disease history 132 to other components of disease prediction system 100, such as diagnoses-based predictor 110. Subject data input interface 316 may comprise various types of interfaces such as, for example, web-based patient input and output (I/O) interface 320, clinician interface 322, health insurance records interface 324, third-party interface 326, and other interfaces 328. Interfaces 320, 322, 324, 326, and 328 may be configured to receive or convert subject-specific disease history 132 from various sources and by various means. For example, subject-specific disease history 132 may be received directly from a user such as the subject, the clinician, the subject's parent or guardian, an insurance company agent, among others. Alternatively, subject-specific disease history 132 may be received through interface 316 through a data conversion interface when used to import data from a pre-existing database containing disease history for a large number of individuals. Furthermore, it is to be understood that in other embodiments of the present invention, subject data input interface 316 may be configured to provide only one of interfaces 320, 322, 324, 326, and 328, as in an embodiment of a special-purpose device, or may be configured to provide multiple interfaces, in another embodiment of a multipurpose prediction system 100. Furthermore, prediction system 100 may be configured to operate as a single system configured to service multiple applications, including self-help home users, insurance company agents, clinicians, etc. as described herein, or may be configured to provide multiple options of interfaces for interfacing a special purpose prediction system 100, as will be described further below with regard to FIGS. 8A-8D.

Figure 4A:
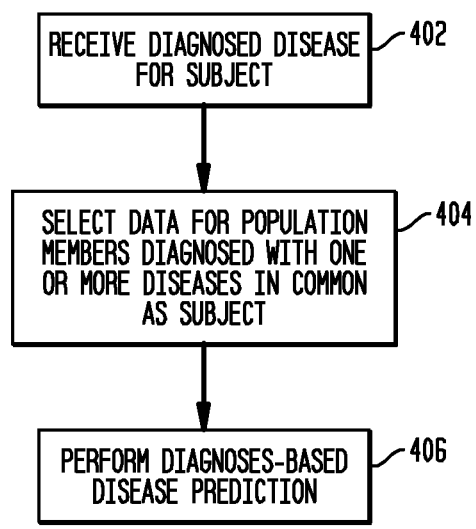
FIG. 4A is a high-level flowchart illustrating one embodiment of the present invention in which diagnoses-based disease predictions are generated.
Figure 4B:
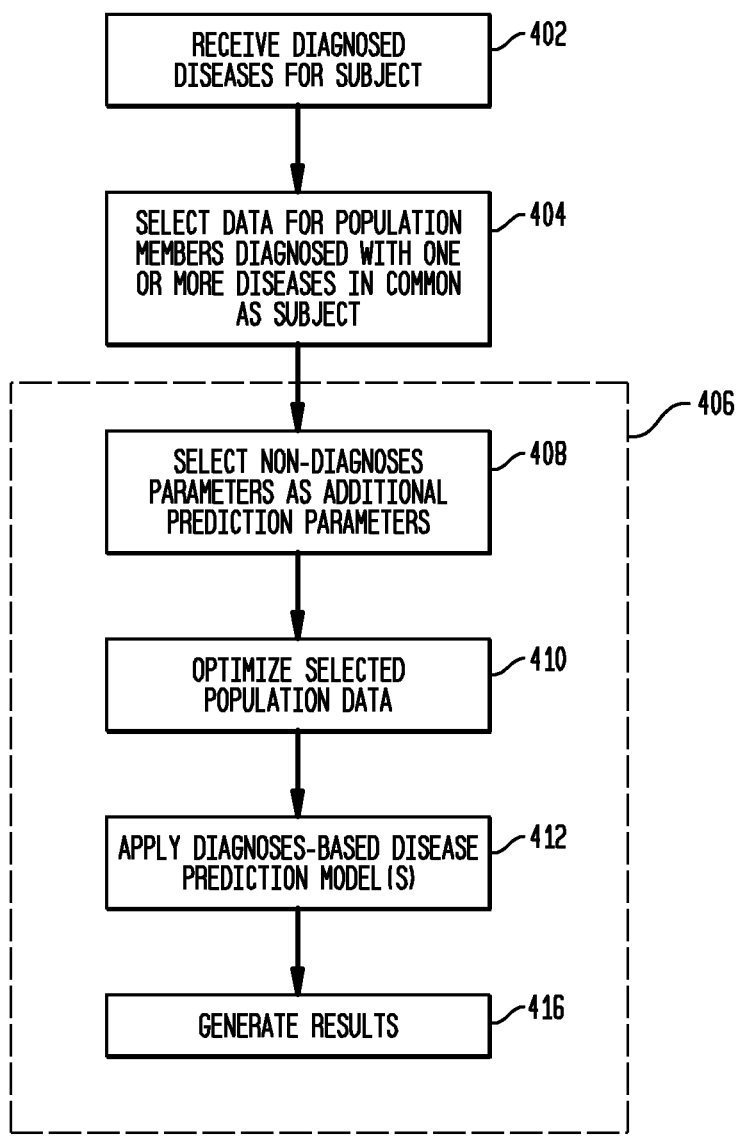
FIG. 4B is a flowchart illustrating one embodiment of the present invention in which diagnoses-based disease predictions are generated.

Flowcharts illustrating one embodiment of the present invention in which diagnoses-based disease predictions are generated are illustrated in FIGS. 4A-4C. FIG. 4A depicts a high-level flowchart illustrating one embodiment of the present invention in which diagnoses-based disease predictions are generated. In box 402, subject-specific disease history 132 is received by prediction system 100. In box 404, members of population diagnosed-disease database 114 are selected based on diseases subject-specific disease history 132, if a member has one or more diagnosed diseases in common with a disease in subject-specific disease history 132. In box 406, one or more prediction models are applied to the other non-common diseases of the selected members to generate raw diagnoses-based disease prediction data 136.

FIG. 4B as well as FIG. 4C provides further details on box 406 of FIG. 4A, illustrating one embodiment of the present invention. In box 408, in addition to selecting population disease diagnostic data 142 at box 404, other data 226 previously described in conjunction with FIG. 2 is also included from population diagnosed-disease database 114. For example, the time of diagnosis for each disease diagnostic data 222 may be included as part of selected population diagnostic data 130. In box 410, selected population diagnostic data 130 is optimized for improved accuracy or efficiency. In one embodiment of the present invention, an inverse frequency function is applied in which lower weights are given to very common diseases, since the sharing of rare diseases between the subject and a population member may provide more interesting or compelling results and therefore should be given more weight, than the sharing of two very common diseases. This inverse frequency for a disease j may be expressed as:

$$f_j = \log\frac{n}{n_j}$$

where n is the number of members in population diagnosed-disease database 114, and $n_j$ is the number of members who have been diagnosed with disease j.

A further optimization technique includes clustering to remove members of population diagnosed-disease database 114 which do not provide any information useful in predicting future diseases for the subject. At its most basic, this clustering excludes all members from population diagnosed-disease database 114 which have no diseases in common with the subject. A benefit from clustering is the reduction in runtime for system 100, as fewer members of database 114 or diseases for those members are compared to subject-specific disease history 132 of the subject. Clustering may further be applied to require a minimum number of diseases to be in common between the members of database 114 and the subject, including the exclusion of specific diseases as the minimum number requirement is being met for each member, thereby reducing the "noise" associated with having too many diseases being predicted despite little similarity between a member of database 114 and the subject's disease history. Based on experimentation, requiring a minimum of three diseases produced favorable results in terms of reduced noise while maintaining accuracy.

A yet further optimization technique includes the collapsing of disease diagnoses into broader categorizations, such as various forms of the International Statistical Classification of Diseases and Related Health Problems ("ICD"). In one embodiment of the present invention, the medical coding system ICD-9 may be implemented whereby diseases are coded according to a predetermined code. In the embodiment, the ICD-9 code of both subject-specific disease history 132 and converted population disease diagnostic data 144 may be collapsed into a more general 3-digit grouping, such that multiple diseases, which may be similar though distinct enough to be coded differently from one another, may be identified by a more general code. By selecting a set of members selected using a more general medical code, instead of by an exact match of the exact disease at issue, and by applying the prediction models on a more general set of medical codes, enhanced or strong similarities and/or patterns may be recognized. As an example, where a particular disease has been identified as belonging to one of fifteen ICD-9 codes, those fifteen codes may be collapsed into codes representing the first three digits of ICD-9 codes, so that many diseases that are similar and have the same first three digits will effectively be viewed as being the same, by having the same first three digits. When those three general codes are used in place of the full ICD-9 code, more members of population diagnosed-disease database 114 will have identically coded diseases and selected as a result. Furthermore, more members of population diagnosed-disease database 114 will have similar collapsed disease codes not among subject-specific disease history 132, such that those similar disease codes may provide enhanced or stronger similarity results, leading to improved diagnoses-based disease prediction in certain cases, as well as simplicity of evaluation and interpretation. In one embodiment of the present invention in which general or collapsed codes are implemented, the specific diagnoses code may be preserved for use in providing the prediction results, even though the collapsed codes are used during the generating of the prediction results. In other embodiments, when diagnoses-based disease prediction data 136 is obtained, information about the collapsed grouping may be provided, or additional analysis may be done use pre-collapse data to determine the exact ICD-9 code to which the intermediate results correlate. Other ICD codes may be used, for example, ICD-9-CM, ICD-10, and ICD-1, to name a few.

After the optimizing step in box 410, box 412 receives the optimized population disease diagnostic data 142 and applies one or more diagnoses-based disease prediction models at diagnoses-based predictor 110, in order to generate diagnoses-based disease predictions at box 416. The one or more diagnoses-based disease prediction models may comprise various models. As used herein, the term "model" describes a sub-system, incorporating one or more formulas or calculations based on set parameters and using one or more inputs to which those formulas or calculations are applied, but may also include a series of steps. A prediction model therefore describes a subsystem for implementing various techniques such as collaborative filtering, artificial neural networks, decision trees, data mining, memory-based model, neighborhood-based model, graph-based model and other artificial intelligence or similar techniques, in order to provide disease predictions according to embodiments of the diagnoses-based prediction system described herein, and are considered a part of the present invention.

For collaborative filtering models, as described above, members of population diagnosed-disease database 114 are selected based on diseases in common with diseases in subject-specific disease history 132. Once the member subset is selected, the disease history of the selected members are analyzed or used in additional computations in order to generate predictions for future diseases for the subject. In one embodiment using a memory-based model, a prediction is generated of the probability p(a, j) that the subject a will experience the onset v of disease j, based on the similarity of members i of population diagnosed-disease database 114 already diagnosed with that disease j. Expressed as a formula, the above model may incorporate the use of:

$$p(a, j) = \overline{v}_j + \kappa(1 - \overline{v}_j)\sum_{i \in I_j} w(a, i).$$

In the above formula, average vote $\overline{v}$ is taken into account for personal differences, as is normalization constant $\kappa$, to ensure that weights are equal to 1. After incorporating the inverse frequency function described above, the similarity w(a,i) between a particular member of population diagnosed-disease database 114 and the subject is represented as:

$$w(a, i) = \sum_j \frac{f_j v_{a,j}}{\sqrt{\sum j \in I_a f_j^2 v_{a,j}^2}} \frac{f_j v_{i,j}}{\sqrt{\sum j \in I_i f_j^2 v_{i,j}^2}}.$$

In addition to the collaborative filtering model described above, neural network models, as is known to persons having ordinary skill in the art, may be designed to take inputs from a large learning dataset, used as training data, and trained to identify missing or future components or steps for a new element provided to the neural network model. Thus, in one embodiment of the present invention, once all members and associated population disease diagnostic data 142 from population diagnosed-disease database 114 is provided to a neural network model implemented in system 100, system 100 will be able to accept and process subject-specific disease history 132 in order to predict or identify disease prediction data 136 of predicted future diseases for the subject. It is to be understood that, although various models have been discussed above with reference to particular formulas and techniques, many other models and associated formulas now known or later developed may be implemented in embodiments of the present invention.

Figure 6:
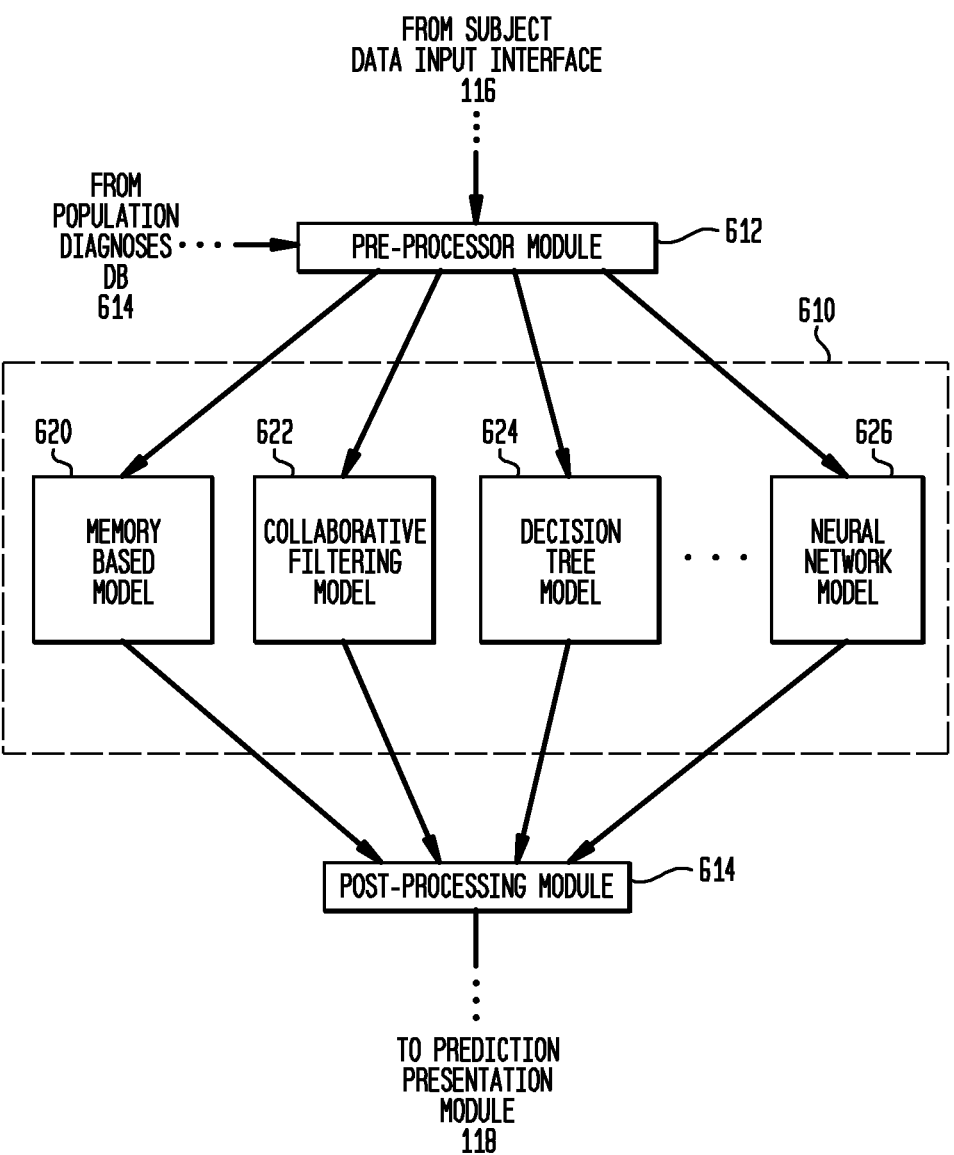
FIG. 6 is a block diagram of a diagnoses-based prediction execution module configured to generate a combined disease prediction based on several prediction models executed simultaneously, in accordance with one embodiment of the present invention.

The models implemented in diagnoses-based predictor 110 described above, as well as other models, may be used individually or collectively, as illustrated in FIGS. 5 and 6. FIG. 5 is a block diagram of a diagnoses-based prediction execution module, in accordance with one embodiment of the present invention. In FIG. 5, diagnoses-based predictor 510 (discussed previously as predictor 110) comprises multiple models including collaborative filtering model 522 and neural network model 526. For a given iteration of prediction system 100, after receiving subject-specific disease history 132, model selector 512 selects a model from those available which will be applied in the iteration. Model selector 512 may base its decision on various factors including reference to a data source or information (not shown) which indicates the optimal model to apply, given the diseases in subject-specific disease history 132. After the optimal model has been selected, selected population diagnostic data 130 may be obtained and used with the selected model to generate one or more disease predictions. Time resolution module 514 receives the disease predictions and, applying time-based information stored as other data 226 in population diagnosed-disease database 114 along with any time-based information for diagnoses in subject-specific disease history 132, generates estimated times for disease onset for each of said diseases predicted for the subject. Alternatively, each of models 522 and 526 may include time resolution functions so that the predictions of disease include time of onset predictions. After the disease predictions, which may include time of disease onset predictions, are generated, the disease predictions are provided to prediction presentation module 118. In addition to selecting and applying a single selected model as discussed above, system 100 may also apply a first model followed by a second model if system 100 determines that the results of the first applied model are insufficient. Furthermore, separate predictions using different models may be generated and provided to a user, for example a researcher or clinician, in order to support or validate the first prediction based on the selected model.

Alternatively, in FIG. 6, diagnoses-based predictor 610 (discussed previously as module 110) applies multiple models. Pre-processor module 612 receives subject-specific disease history 132 as well as selected population diagnostic data 130 and provides history 132 and data 130 to select or all available models. Where history 132 and data 130 is provided to select models, pre-processor module 612 selects the appropriate models based on the diseases contained in selected population diagnostic data 130, based on reference to experimental and design information (not shown) regarding each model and their particular strengths and weaknesses for analyzing or making predictions based on particular diseases. Additionally, pre-processor module 612 may determine weighting values such that the predictions generated for particular diseases in selected population diagnostic data 130 may later be assigned different weights, in order to generate an optimal prediction. Post-processing module 614 receives the prediction data from each of the models applied, for example models 622 and 626, and processes them according to pre-set parameters and/or those set by pre-processor module 612, such as applying the weights to each prediction data as set by pre-processor module 612. Once the prediction data has been processed by post-processing module 614 into a set of raw diagnoses-based disease prediction data 136, the prediction data 136 is provided to prediction presentation module 118.

FIGS. 7A-7B are simplified screen shots of subject data input interfaces, in accordance with one embodiment of the present invention. In FIG. 7A, first input interface 730 comprises various selections and input fields, such as field 732 for the subject's name and selectable button 734, used in the embodiment shown to select the method of inputting a particular disease of the subject. It is to be understood that first input interface 730 may comprise various other inputs which a user, such as the subject or the subject's parent or guardian, a clinician, an insurance company agent, a researcher, etc. may use to input various types of data described above, such as disease diagnostic data, demographic data, etc. for use in prediction system 100.

Similarly, in FIG. 7B, second input interface 736 comprises various fields and selectable icons which a user may use to input various information for use in prediction system 100. For example, an ICD coding format (e.g., ICD-9) may be selected by the user using field 740. Once the desired ICD code has been selected, the user may input an ICD code in field 742 and then activate "search" button icon 744. Alternatively, the user is given an option to navigate to the desired ICD code by using the navigation menu to the right of input interface 736. As shown in FIG. 7B, the various ICD-9 codes categories (e.g., 101-200) shown are all collapsed, but may be navigated by expanding the plus symbols 746, and further selecting or expanding the options which appear.

Figure 7C:
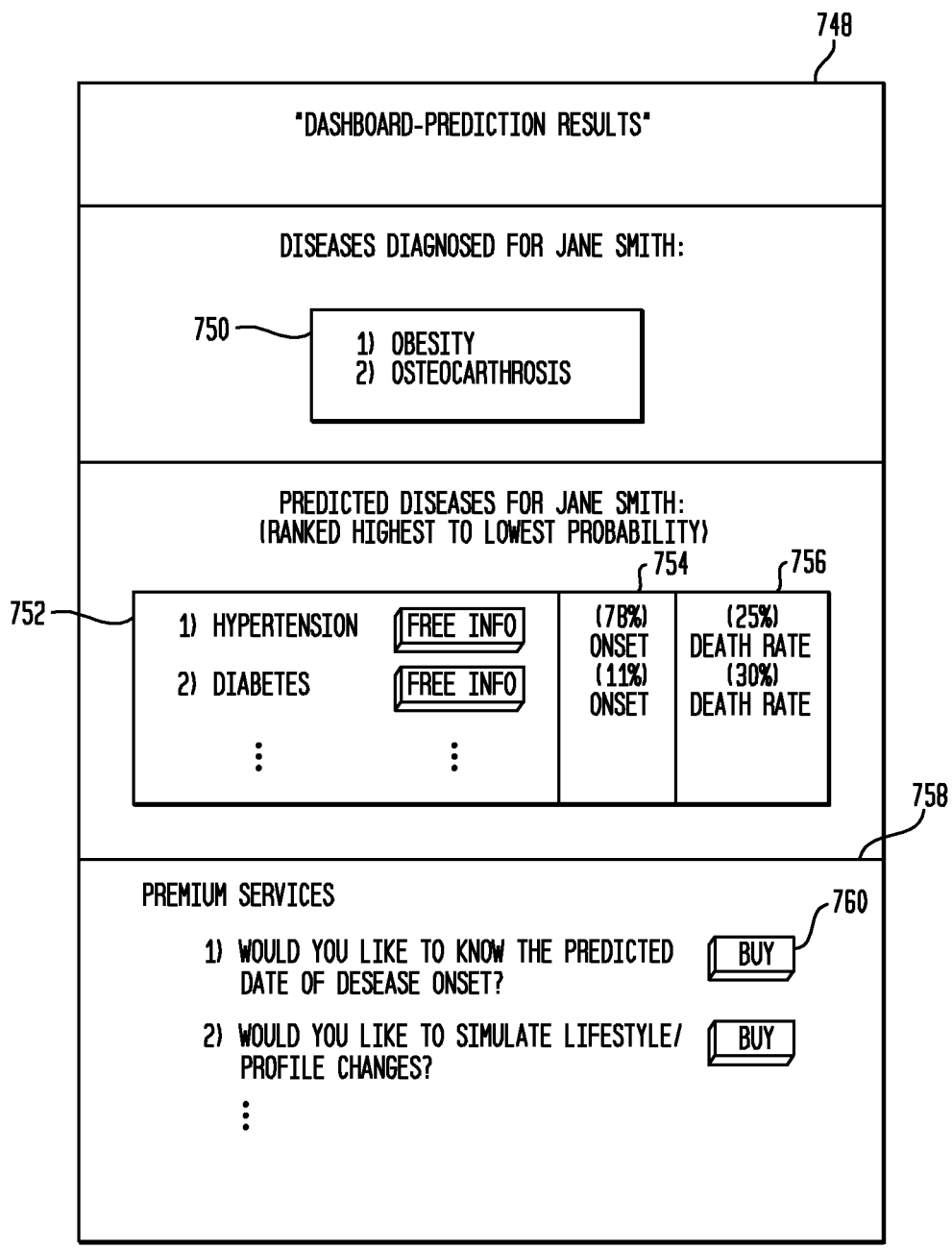
FIG. 7C is a simplified display of a diagnoses-based disease prediction results interface, in accordance with one embodiment of the present invention.

FIG. 7C is a simplified screen shot of a diagnoses-based disease prediction results interface 748, in accordance with one embodiment of the present invention. Results interface 748 is shown in FIG. 7C as comprising various regions. Region 750 displays subject-specific disease history 132 provided by the user about the subject. Prediction window 752 comprises the diseases predicted for the subject as well as region 754, displaying the probability of onset for each predicted disease, and region 756, displaying the mortality rate for each predicted disease. In addition to the predicted disease, prediction window 752 may display buttons that may be selected by the user to obtain additional information, such as free generic information not displayed in prediction window 752. Additionally, in commercial embodiments of the present invention, the user may purchase additional information or services 760, such as medical advice customized for the subject, given subject-specific disease history 132 already entered or additional information which may be subsequently entered via an information form or interactive interview (not shown), as will be further described below with reference to specific applications of diagnoses-based disease prediction system 100.

Figure 8C:
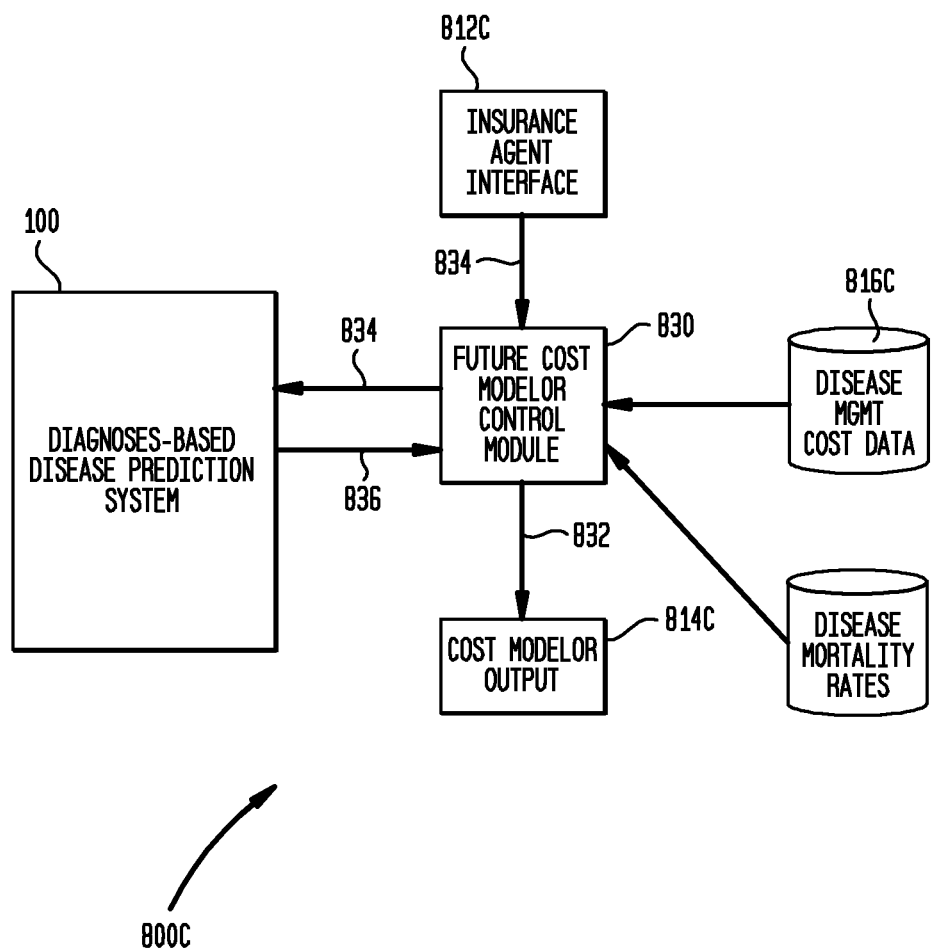
FIG. 8C is a block diagram of a disease management cost modeler application of the diagnoses-based disease prediction system illustrated in FIG. 1, according to one embodiment of the present invention.

FIGS. 8A-8D are block diagrams of specific applications of the diagnoses-based disease prediction system illustrated in FIG. 1, according to various embodiments of the present invention. FIG. 8A depicts a clinician prediction system 800A incorporating diagnoses-based disease prediction system 100. In one embodiment of the present invention, clinician prediction system 800A comprises a clinician control module 810 which coordinates data between the various components of system 800A. Input data 814 from a clinician is received via clinician input interface 812A and provided to prediction system 100 via subject data input interface 116. The results data 818 (previously discussed as organized results data 138) is received by clinician control module 810 and used to retrieve information from lab test database 816A about applicable laboratory tests which the subject should perform in order to monitor and possibly treat the predicted disease or precursors thereof. The prediction results and recommended laboratory tests, shown in FIG. 8A as diagnoses-based disease prediction clinician results data 813, are printed or otherwise provided to the clinician by clinician output 814A for review with the subject.

FIG. 8B depicts a risk factor simulation system 800B, incorporating diagnoses-based disease prediction system 100. In one embodiment of the present invention, risk factor simulation system 800B comprises a risk factor simulator 820 which coordinates data between the various components of system 800B. Input data 824 from a user such as a clinician or counselor is received via simulator input interface 812B and provided to prediction system 100 via subject data input interface 116. The results data 818 (previously discussed as organized results data 138) is received by clinician control module 820 and printed or otherwise provided to the operator by simulator output 814B for review. Commercial embodiments of system 800B may also comprise a customer management system 838 and customer database 839 to track, manage and receive payments from customers of system 800B. Similar CMS and customer databases may be incorporated with other specific applications of disease prediction system as described herein.

FIG. 8C depicts a future cost modeling system 800C, incorporating diagnoses-based disease prediction system 100. In one embodiment of the present invention, future cost modeling system 800C comprises a future cost modeling control module 830 which coordinates data between the various components of system 800C. Input data 834 from a user such as a clinician or counselor is received via insurance agent input interface 812C and provided to prediction system 100 via subject data input interface 116. The results data 836 (previously discussed as organized results data 138) is received by future cost modeling control module 830 and combined with cost data from disease management cost database 816C and/ or disease mortality rate database 836 in order to generate diagnoses-based disease predicted cost results 832 which is provided to cost modeler output 814C for review by the insurance agent.

Figure 8D:
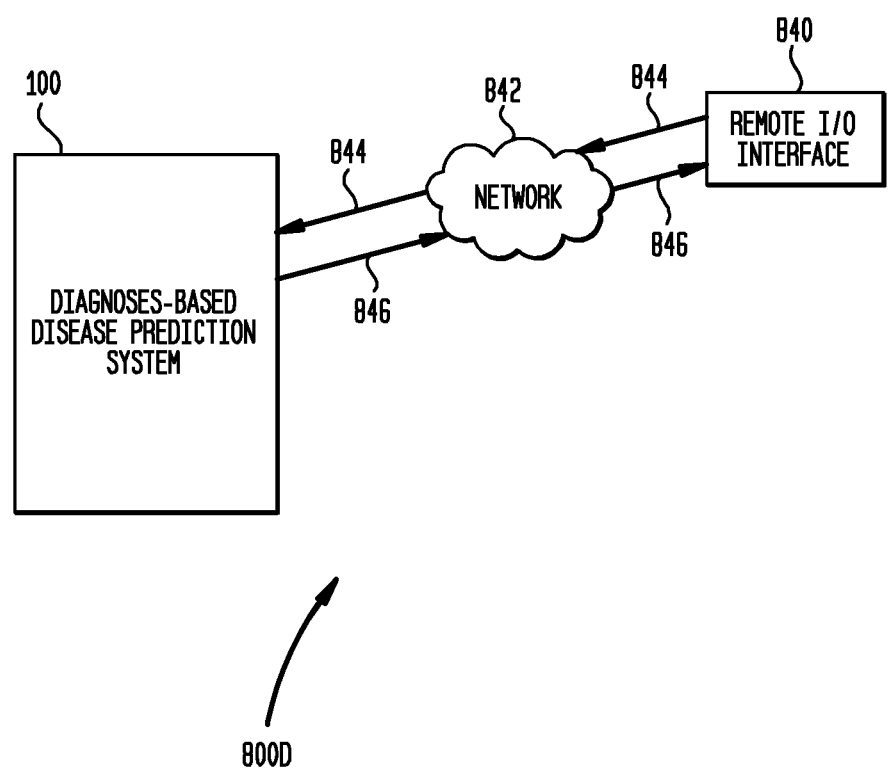
FIG. 8D is a block diagram of a remote access application of the diagnoses-based disease prediction system illustrated in FIG. 1, according to one embodiment of the present invention.

In yet another embodiment of the present invention, FIG. 8D depicts a remote access diagnoses-based disease prediction system 800D in which a user is able to operate prediction system 100 remotely, through remote input/output (I/O) interface 840. In remote access system 800D, a user provides input data 844 via remote I/O interface 840. Input data 844 is passed through a network, such as the Internet or a local area network (LAN) to prediction system 100. Results data 846 (previously discussed as organized results data 138) is provided by prediction system 100 as described above, through network 842 and returned to remote I/O interface 840. Although not shown in FIG. 8D, it is to be understood that in addition to communication hardware in network 842, customer management systems, customer databases, and payment systems may be present along or via network 842 in order to allow commercial operations surrounding prediction system 800D, according to one embodiment of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom. Furthermore, although various components and hardware, for example storage area networks ("SAN") and computer systems, and components thereof, have been described in conjunction with specific embodiments of the present invention, it should be understood that the embodiments of the present invention should not be limited to the features of those exemplary embodiments, and that other embodiments of the present invention may be implemented having components physically together or remote with respect to one another. Furthermore, as one of ordinary skill in the art would appreciate, although various exemplary data and other exemplary communications between the various components of various embodiments have been described above, it should be understood that other embodiments of the present invention may use different types of communications to implement the present invention.

What is claimed is:

1. A computer system for predicting future disease for a subject comprising:
 a database comprising a population information set comprising population disease diagnoses for members of a population;
 the database further comprising a subject-specific information set comprising at least one subject-specific disease diagnosis corresponding to a past-diagnosed disease of said subject;
 a processor configured to execute modules comprising at least:
 an optimization module configured to select a diagnosed disease subset of the members of the population, wherein said diagnosed disease subset includes members of the population that have at least one diagnosed disease in common with the past-diagnosed disease of said subject;
 a diagnoses-based prediction module configured to predict one or more future diseases for the subject by comparing said subject with the diagnosed disease subset of the members of the population;
 wherein the diagnoses-based prediction module predicts the one or more future diseases for the subject by applying a collaborative filtering model, wherein the collaborative filtering model accounts for a similarity between a particular member of the diagnosed disease subset of the members of the population and the subject by using an inverse frequency function configured to assign a low weight to common diseases and a high weight to rare diseases; and
 an output interface for outputting the predicted one or more future diseases for the subject.

2. The computer system of claim 1, wherein the population information set further comprises:
 at least one non-diagnosis of a disease for one or more members of the population.

3. The computer system of claim 1, wherein said population information set and said subject-specific information set each further comprise:
 demographic data for one or more members of the population.

4. The computer system of claim 3, wherein said demographic data comprises one or more of birth date, sex, ethnicity, and geographic data for one or more members of the population.

5. The computer system of claim 1, further comprising:
 a subject data input interface configured to receive said subject-specific disease diagnosis and further configured to provide the received subject-specific disease diagnosis to said diagnoses-based prediction module.

6. The computer system of claim 1, wherein said diagnoses-based prediction module implements additional prediction models of the group consisting of a memory-based model, a decision-tree-based model, a data mining model, a neighborhood-based model, a graph-based model, and a neural network model to generate said disease prediction.

7. The computer system of claim 1, further comprising:
 a population information set conversion module, configured to receive medical information from one or more sources and further configured to convert the received medical information into a preset format for input into the database.

8. The computer system of claim 1, further comprising:
 a lab test database comprising lab test information for a plurality of diseases; and
 a clinician control module configured to retrieve lab test information from said lab test database,
 wherein said clinician control module is configured to receive input from a clinician and to provide the received inputs to said diagnoses-based prediction module, and further wherein said clinician control module receives lab test information from said lab test database that determine said one or more future disease predictions received from said diagnoses-based prediction module.

9. The computer system of claim 1, further comprising:
 a risk factor simulator configured to receive modifications to said at least one subject-specific disease diagnoses and to request one or more future disease predictions from said diagnoses-based prediction module.

10. The computer system of claim 1, further comprising:
 a future cost modeler; configured to calculate a cost estimate for the one or more future diseases generated by the diagnoses-based prediction module; and
 a disease management database module comprising disease management cost data for a plurality of diseases, configured to provide said cost data to said future cost modeler for said one or more future diseases in said disease prediction.

11. The computer system of claim 1, further comprising:
a remote user interface configured to be communicatively coupled with said diagnoses-based prediction module over a network connection,
wherein said remote user interface is configured to provide user input to said diagnoses-based prediction module and to reproduce said one or more disease predictions received from said prediction module.

12. The computer system of claim 1, wherein said population information set further comprises:
a time of diagnosis for one or more diagnostic data for one or more of the population members, and
further wherein said diagnoses-based prediction module further comprises:
a time prediction module configured to predict a time of onset of when a disease is predicted to occur in the subject by analyzing said population information set.

13. The disease prediction system of claim 1, wherein said optimization module is configured to collapse International Statistical Classification of Diseases and Related Health Problems codes corresponding to said population disease diagnoses and said subject-specific disease diagnosis into generic codes.

14. The computer system of claim 6, wherein said diagnoses-based prediction module is configured to simultaneously process one or more of the prediction models to generate a disease prediction from each prediction model, and further configured to combine each of said disease prediction into a combined disease prediction.

15. The computer system of claim 14, wherein said diagnoses-based prediction module is configured to generate the combined disease prediction by weighting the disease predictions generated from the prediction models.

16. The computer system of claim 1, wherein said system is further configured to provide other information about said disease prediction, wherein said other information comprises at least one of mortality rates, educational information, links to information, coupons, and documents.

17. The computer system of claim 1, wherein the diagnosed disease subset of the members of the population comprises only members of the population that have at least three diseases in common with the subject and excludes members of the population that have less than three diseases in common with the subject to reduce data noise.

18. The computer system of claim 1, wherein said diagnosed disease subset includes only members of the population that have at least one diagnosed disease in common with the past-diagnosed disease of said subject.

19. A computer-implemented method for predicting future disease for a subject by analyzing a population information set containing population disease diagnoses for members of a population; and a subject-specific information set containing at least one subject-specific disease diagnosis, comprising:
accessing computer-executable instructions from at least one computer-readable storage medium; and
executing the computer-executable instructions, thereby causing computer hardware comprising at least one computer processor to perform operations comprising:
accessing a database comprising a population information set comprising population disease diagnoses for members of a population, the database further comprising a subject-specific information set comprising at least one subject-specific disease diagnosis corresponding to a past-diagnosed disease of said subject;
selecting a diagnosed disease subset of the members of the population, wherein said diagnosed disease subset includes members of the population that have at least one diagnosed disease in common with the past-diagnosed disease of said subject;
generating one or more disease predictions for the subject by applying a collaborative filtering model, wherein the collaborative filtering model accounts for a similarity between a particular member of the diagnosed disease subset of the members of the population and the subject by using an inverse frequency function configured to assign a low weight to common diseases and a high weight to rare diseases; and
outputting the predicted one or more disease predictions.

20. The computer-implemented method for predicting future disease of claim 19, further comprising:
sorting said one or more disease predictions in order of highest to lowest probability of onset in the subject.

21. The computer-implemented method for predicting future disease of claim 19, wherein the population information set also contains at least one demographic data for the members, and further wherein said generating one or more disease predictions further comprises:
selecting a demographic data for the members of the population; and
applying said selected demographic data to generate said one or more disease predictions.

22. The computer-implemented method for predicting future disease of claim 19, wherein the population information set also contains non-diagnosis of a disease for the members, and further wherein said generating one or more disease predictions further comprises:
selecting at least one non-diagnosis information for the members of the population; and
applying said selected non-diagnosis information to generate said one or more disease predictions.

23. The computer-implemented method for predicting future disease of claim 19, wherein said generating one or more disease predictions for the subject further comprises:
applying one or more diagnosis-based prediction models to the diagnoses information about members of a population and a subject to generate said one or more disease predictions.

24. The computer-implemented method for predicting future disease of claim 23, wherein the diagnosis-based prediction module implements additional prediction models of the group consisting of a memory-based model, a decision-tree-based model, a data mining model, a neighborhood-based model, a graph-based model, and a neural network model to generate said disease prediction.

25. The computer-implemented method for predicting future disease of claim 24, further comprising:
applying the one or more prediction models simultaneously to generate a disease prediction from each applied prediction model; and
combining each of the disease predictions from each model to generate a combined disease prediction.

26. The computer-implemented method for predicting future disease of claim 25, wherein combining each of the disease predictions comprises:
weighting each of the disease predictions from each model according to a predetermined weighting scheme.

27. The computer-implemented method for predicting future disease of claim 19, further comprising:
converting the population disease diagnoses from at least one information source into a preset format; and
appending said converted population disease diagnoses to the population information set.

28. The computer-implemented method for predicting future disease of claim 19, further comprising:
converting the subject-specific diagnosis information into a preset format; and
appending said converted subject-specific diagnosis information to the population information set.

29. The computer-implemented method for predicting future disease of claim 19, further comprising:
changing the subject-specific diagnosis information; and
simulating a change in the disease prediction by generating the disease prediction from the changed subject-specific diagnosis information.

30. The computer-implemented method for predicting future disease of claim 19, further comprising:
retrieving one or more cost data for managing one or more diseases in the generated one or more disease predictions.

31. The computer-implemented method for predicting future disease of claim 19, further comprising:
receiving the subject-specific disease diagnosis from a remote user interface; and
providing the generated one or more disease predictions to the remote interface.

32. The computer-implemented method of claim 19, wherein the diagnosed disease subset of the members of the population comprises only members of the population that have at least three diseases in common with the subject and excludes members of the population that have less than three diseases in common with the subject to reduce data noise.

33. The computer-implemented method of claim 19, wherein said diagnosed disease subset includes only members of the population that have at least one diagnosed disease in common with the past-diagnosed disease of said subject.

* * * * *

UNITED STATES PATENT AND TRADEMARK OFFICE
CERTIFICATE OF CORRECTION

PATENT NO. : 8,504,343 B2  Page 1 of 1
APPLICATION NO. : 12/023935
DATED : August 6, 2013
INVENTOR(S) : Chawla et al.

It is certified that error appears in the above-identified patent and that said Letters Patent is hereby corrected as shown below:

On the Title Page (item 54, Title) at line 1, and in the Specification, in column 1 (Title) at line 1, Change "BASES" to --BASED--.

In the Drawings
Sheet 9 of 14 (Reference Numeral 734, FIG. 7A) at line 1, Change "1CD" to --ICD--.
Sheet 9 of 14 (Reference Numeral 740, FIG. 7B) at line 1, Change "1CD-9" to --ICD-9--.
Sheet 9 of 14 (Reference Numeral 740, FIG. 7B) at line 1, Change "1CD-10" to --ICD-10--.
Sheet 10 of 14 (Reference Numeral 750, FIG. 7C) at line 2, Change "OSTEOCARTHROSIS" to --OSTEOARTHRITIS--.
Sheet 10 of 14 (Reference Numeral 754, FIG. 7C) at line 1, Change "(7B%)" to --(78%)--.

In the Specification
In column 4 at line 11, Change "and or" to --and/or--.
In column 9 at line 36 (approx.), Change "ICD-1," to --ICD-11,--.

In the Claims
In column 14 at line 60, In Claim 10, Change "modeler;" to --modeler--.

Signed and Sealed this
Tenth Day of June, 2014

Michelle K. Lee
*Deputy Director of the United States Patent and Trademark Office*